United States Patent [19]

Losi

[11] Patent Number: 4,878,615
[45] Date of Patent: Nov. 7, 1989

[54] FLUID EVAPORATING DEVICES
[75] Inventor: Salvatore A. Losi, Petit-Lancy, Switzerland
[73] Assignee: Givaudan Corporation, Clifton, N.J.
[21] Appl. No.: 196,414
[22] Filed: May 20, 1988
[30] Foreign Application Priority Data
  May 25, 1987 [CH] Switzerland .......................... 2012/87
[51] Int. Cl.⁴ ............................................... A61L 9/04
[52] U.S. Cl. ....................................... 239/45; 239/47; 239/51.5; 239/57; 239/59
[58] Field of Search ..................... 239/34, 45, 47, 51.5, 239/57, 58, 59; 222/207, 211

[56] References Cited
U.S. PATENT DOCUMENTS

| | | | |
|---|---|---|---|
| 3,246,807 | 4/1966 | Micallef | 222/207 |
| 3,447,907 | 6/1969 | Bennett | 239/51.5 X |
| 4,200,229 | 4/1980 | Spector | 239/57 |
| 4,474,312 | 10/1984 | Donoghue | 222/207 X |
| 4,477,414 | 10/1984 | Muramoto et al. | 239/44 |
| 4,732,321 | 3/1988 | Dolan | 239/45 |
| 4,762,275 | 8/1988 | Herbert et al. | |
| 4,768,676 | 9/1988 | Kaneko | 239/44 X |

FOREIGN PATENT DOCUMENTS
1174963 9/1984 Canada .
78114 5/1983 European Pat. Off. .
214918 3/1987 European Pat. Off. .
2486402 1/1982 France .

Primary Examiner—Andres Kashnikow
Assistant Examiner—Patrick N. Burkhart
Attorney, Agent, or Firm—Robert F. Tavares; Linda A. Vag

[57] ABSTRACT

Method and apparatus for the evaporation of a solution into the ambient air. The apparatus contains a reservoir having at least one elastic wall; a first compartment outside the reservoir having an opening to the ambient air; a passage which may be intermittently opened and closed, connecting the reservoir to the first compartment; and, an absorbent material placed on a support which is outside both the reservoir and the first compartment, and which is in contact with the first compartment. By exerting pressure on the elastic wall of the reservoir, solution may be transferred from the reservoir to the first compartment through the passage when it is open. The passage is kept closed during the time intervals between intermittent transfers of the solution. The portion of solution which has been transferred to the first compartment is gradually and continuously transferred to the absorbent material for evaporation to the ambient air.

11 Claims, 4 Drawing Sheets

FLUID EVAPORATING DEVICES

BACKGROUND OF THE INVENTION

1. Field of the Invention
Fluid evaporating devices.

2. Background Art

Fluid evaporating devices, which employ a wick to conduct a fragrance material from an isolated reservoir containing the liquid to the ambient air, are well known in the art. The fragrance material may be allowed to evaporate from the exposed end of the wick per se, or the wick may be used to conduct the liquid to a water-absorbent material, whereby the fragrance is allowed to evaporate into the ambient air from the exposed surface of the absorbent material. In either case, the wick is immersed directly into the fragrance material contained in the reservoir. Fluid evaporating devices of this type have been found to suffer from the disadvantage that the more volatile components of the fragrance material are removed first, leaving the less volatile components behind. This change in composition with time eventually results in a distortion in the odor and weakening in the intensity of the fragrance, since the less volatile component evaporates more slowly. The odor of the fragrance material becomes very weak after only a short period of time, usually after a week or two of use.

Various devices have been developed in order to overcome these limitations, i.e., distortion and weakening of the odor of the fragrance material. Aerosol-type systems have been developed which will maintain fragrance integrity over their useful life, but have the disadvantage they are useful only while they are being sprayed and unless constantly sprayed, they lose their effectiveness in a few minutes. Mechanical devices have been developed to introduce a premeasured amount of the fragrance material into the ambient air, at regularly timed intervals. These devices are usually electrically or battery operated and complex in design. Devices have been developed which will continuously transfer the fragrance material from a reservoir to a second chamber, which contains the wick-type delivery system. These devices are designed such that they operate continuously once started and cannot be interrupted.

The fluid evaporating device and method of the present invention overcome the limitations of the conventional wick systems of the prior art, i.e., distortion and weakening of the fragrance over the life span of the device, while avoiding the complexity and other drawbacks of the above prior art devices. The device is simple in design, and employs a delivery system which allows the user to interrupt the flow of the liquid from the reservoir and to hermetically seal the fragrance material from the ambient air, whenever it is desired to do so, without taking the device apart.

SUMMARY OF THE INVENTION

The present invention concerns a method and device for evaporating multi-component fragrance materials into the ambient air, at a steady rate, without having the fragrance become weak or distorted over a period of time. The device may be used to dispense other multi-component solutions, such as insecticides, bacteriocides, mold inhibitors, and the like.

The device, in its simplest form, is comprised of a container which acts as a reservoir for holding the solution to be evaporated, a separate compartment to which a desired portion of the solution to be evaporated is transferred and which is in contact with an absorbent material outside the compartment from which the fragrance may evaporate to the ambient air, a passage connecting the reservoir and the compartment, and means for opening and closing the passage. The transfer of the fragrance material through the open passage may be accomplished by exerting pressure on the container, which has at least one elastic side. When the passage is closed, the fragrance material in the reservoir is hermatically sealed from the ambient air.

More specifically, the device comprises:

(a) a reservoir designed to contain a certain volume of a solution, said reservoir having at least one elastic wall;

(b) a first compartment outside said reservoir, said first compartment having an opening to the ambient air;

(c) a passage for the transfer of a portion of said solution from said reservoir to said first compartment;

(d) means for opening and closing, respectively, said passage for said transfer of said portion of said solution, thereby permitting and preventing, respectively, said transfer;

(e) an impregnation member placed on a support outside said reservoir and outside said first compartment; and (f) means for gradually and continuously transferring the solution contained in said first compartment to said impregnation member.

A preferred embodiment of the device also comprises means for opening and closing, respectively, said opening of said first compartment to the ambient air.

The invention also concerns a method for the evaporation of a solution to the ambient air which comprises:

(a) introducing a certain volume of a solution into a reservoir having at least one elastic wall;

(b) intermittently opening a passage connecting said reservoir and a first compartment outside said reservoir for the transfer of a portion of said solution from said reservoir to said first compartment;

(c) exerting an external pressure on said elastic wall of said reservoir, when said passage is open, sufficient to transfer a portion of said solution contained in said reservoir to said first compartment, and gradually and continuously transferring a portion of the solution contained in said first compartment to an impregnation member consisting of a material capable of absorbing a liquid, said member being placed on a support outside said reservoir and outside said first compartment; and (d) closing said passage, and keeping it closed during the time intervals between the intermittent transfers of portions of said solution from said reservoir to said first compartment.

A preferred embodiment of the method also comprises:

(a) intermittently opening an opening in said first compartment to the ambient air;

(b) exerting an external pressure on said elastic wall of said reservoir, when said opening and said passage are open, sufficient to transfer said portion of said solution from said reservoir to said first compartment;

(c) closing said opening of said first compartment and closing said passage; and (d) keeping said opening and said passage closed during the time intervals between intermittent transfers of portions of said solution.

The advantages obtained by the use of the fluid evaporating device of this invention consist essentially in that the evaporation of the solution takes place while a constant proportion of its components is preserved virtually throughout the period of use of the evaporating apparatus, the device may be used intermittently or continuously, as desired by the user, it is possible to achieve hermetic sealing of the reservoir for transporting the apparatus without the need to disassemble the apparatus, the simplified and compact structure of the apparatus enables it to be inexpensively manufactured.

DETAILED DESCRIPTION OF THE INVENTION

Figure 1:
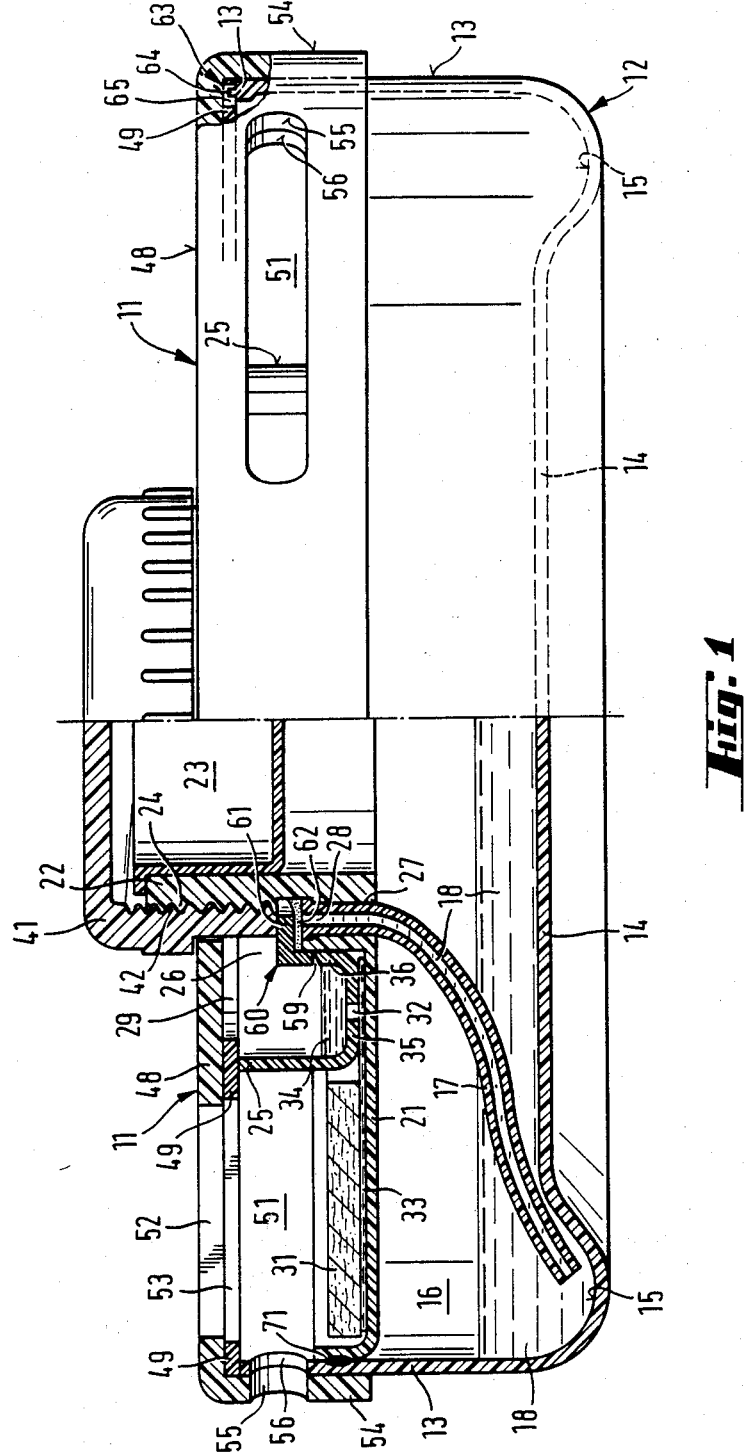
FIG. 1 illustrates a partially sectional view of an apparatus according to the invention.

The evaporating device shown in FIG. 1 comprises a vessel 12 and a lid 11. The vessel 12 is cylindrical in shape and has side walls 13 and a bottom 14. The vessel 12 is manufactured as a flexible and elastic plastic, for example, by molding semi-transparent polyethylene through an injection blow molding process.

The vessel 12 comprises a support plate 21, which divides the inside of the vessel into a lower portion and an upper portion. The lower portion of the vessel, enclosed between the support plate 21 and the base 14 of the vessel, forms a reservoir 16 designed to receive a certain volume of the solution 18 to be evaporated. A connection 71 between the plate 21 and the wall 13 prevents flow of liquid between the peripheral outer wall of plate 21 and the wall 13.

The support plate 21 contains a neck 22 which extends upwards from its central portion. This neck 22 is the neck of the reservoir 16. The neck 22 is normally closed by a plug 23 which is driven into place. It is hence necessary to remove this plug when it is desired to introduce the solution to be evaporated into the reservoir 16.

Figure 2:
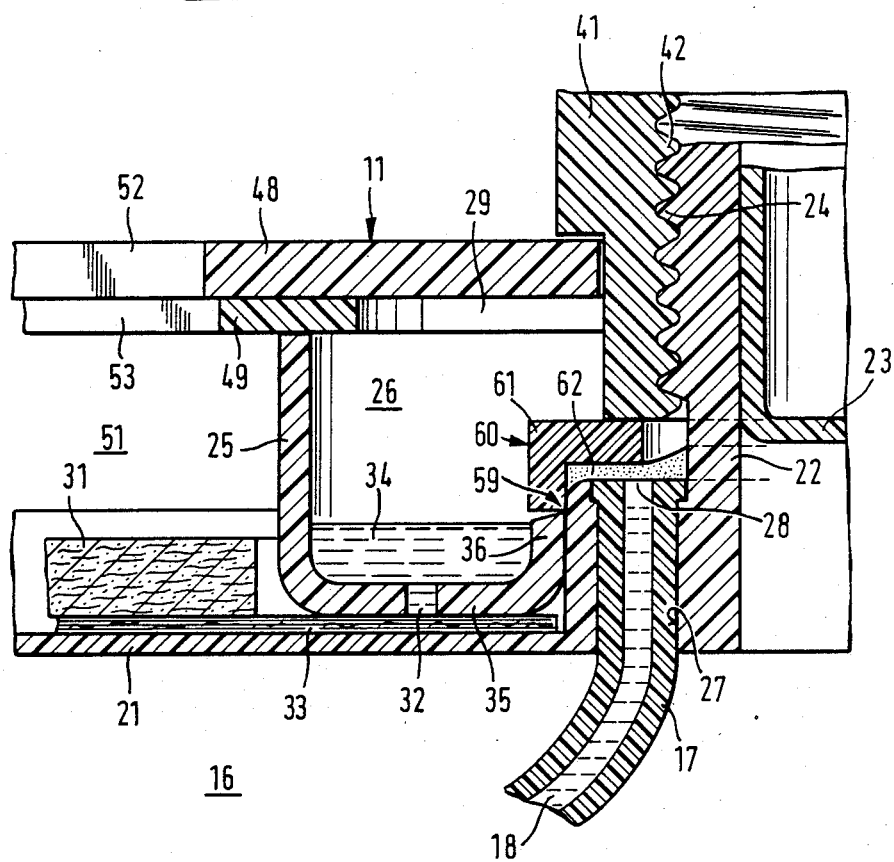
FIG. 2 illustrates an enlarged sectional view of the central portion of the apparatus according to FIG. 1. In this view, the passage (17, 28) is closed by the plug 41 which is a part of the lid 11 in FIG. 1.
Figure 3:
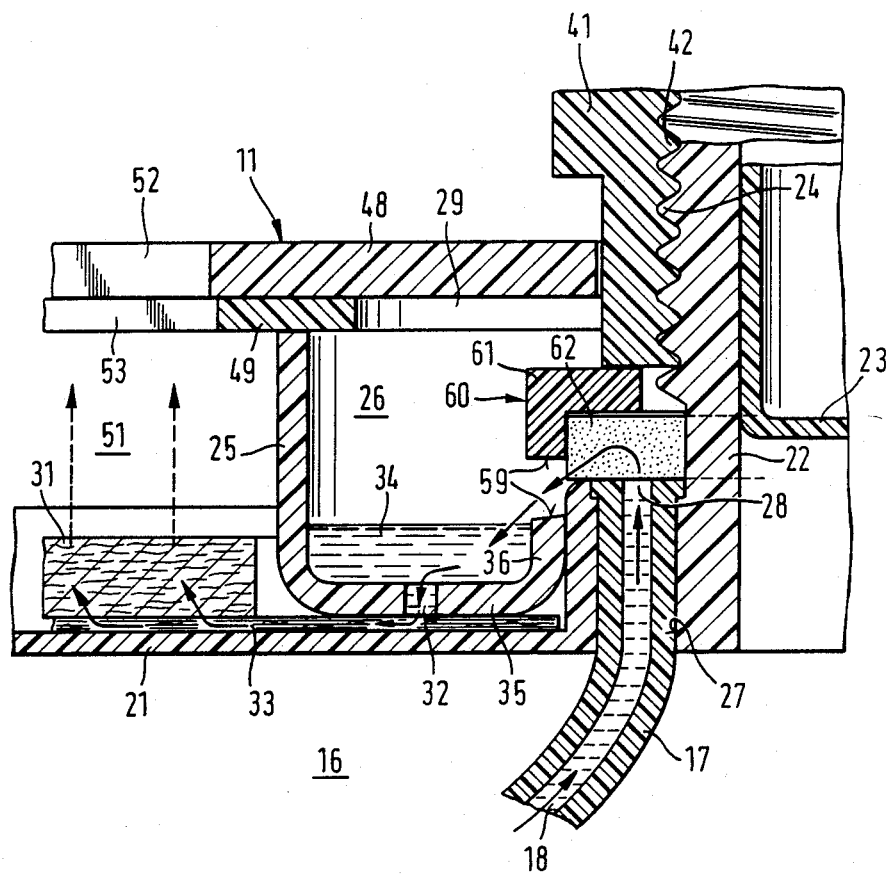
FIG. 3 illustrates an enlarged sectional view similar to that shown in FIG. 2, but showing the plug 41 in a position in which it does not close the passage (17, 28) in FIG. 2.

As shown schematically in FIG. 1, and in greater detail in FIGS. 2 and 3, the space enclosed between the outer side wall 13 of the vessel 12 and the neck 22 in the upper portion of the vessel is divided into two compartments. A first compartment 26 is bound by a cylindrical outer wall 25, the outer wall of the neck 22, an inner cylindrical wall 36, and a base wall 35. The remainder of the upper portion of the vessel forms a second compartment 51.

An annular impregnation member 51 is mounted in the outer compartment 51 on the support plate 21. The impregnation member 31 consists of a material, such as filter paper made of natural fibers or synthetic fibers, which is capable of absorbing a liquid such as water.

A layer 33 is placed between the base wall 35 of the compartment 26 and the support plate 21 in contact with the impregnation member 31. The layer 33 is made of a fibrous material capable of absorbing a liquid, such as water and acts as a capillary wick.

The base wall 35 of the compartment 26 has an orifice 32, which brings the inside of the compartment 26 into communication with the layer 33 of fibrous material.

The compartment 26 has a opening 29, which brings the inside of the compartment 26 into direct communication with the atmosphere when it is open. In the position of the lid 11 illustrated in FIG. 2, the opening 29 is closed by the portion 48 of the lid 11. In the position of the lid shown in FIG. 3, the lid has been moved slightly upwards and the opening 29 is open.

The support plate 21 has a bore 27, which passes through this plate in a portion of the latter enclosed between the neck 22 and the cylindrical wall 36 of the compartment 26.

A feed tube 17 placed in the reservoir 16 is provided for transferring a portion of the solution 18 from the reservoir 16 to the compartment 26. The tube 17 extends between a point close to the bottom 14 of the vessel 12 and the bore 27. The upper end of the tube 17 is inserted into the bore 27. The lower end of the tube 17 is preferably arranged in a cavity 15 formed in the bottom 14 of the vessel 12.

In its upper end, the feed tube 17 has an orifice 28 which is at the same level as the upper end of the bore 27. The orifice 32, in the base wall 35 of the compartment 26, is at a level below the level of the upper end of the bore 27 and of the orifice 28 of the feed tube 17. During the transfer of a portion of the solution 18 from the reservoir 16 to the compartment 26, the orifice 28 functions as an overflow orifice, i.e., if the volume transferred is excessive with respect to the level of the orifice 28, the portion of the liquid volume in excess above this level returns to the reservoir 16 through the orifice 28.

The volume of solution 34 contained in the compartment 26 flows through the orifice 32 to the layer of fibrous materials 33 and thence to the impregnation member 31. Since the layer 33 transports the solution by capillarity, the transfer of the solution from the compartment 26 to the impregnation member 31 takes place gradually and continuously.

The support plate 21, as well as the walls of the compartment 26, are manufactured as a flexible and elastic plastic, for example, by molding semi-transparent polyethylene through an injection blow molding process.

A removable annular disk 49 is inserted between the vessel 12 and the lid 11. The disk 49 bounds the upper portion of the outer compartment 51, and has windows 53. This disk is preferably transparent and rigid and is made, for example, by molding polymethyl methacrylate through an injection molding process. The disk 49 is pinned onto the upper edge of the vessel 12 and is hence firmly attached to the latter.

The lid 11 contains a plug 41 and an annular disk 48, which has a cylindrical flange 54. The plug 41 is preferably manufactured as a flexible plastic, for example, by molding polyethylene by an injection blow molding process. The annular disk 48 is preferably transparent and is manufactured as a rigid plastic, for example, by molding polymethyl methacrylate in an injection molding process.

The plug 41 has an internal thread 42 enabling this plug to be screwed on the neck 22, which has an external thread 24 which corresponds to the internal thread of the plug 41.

The arrangement of various constituent parts of the evaporating apparatus is such that, when the plug 41 is screwed on the neck 22, an hydraulic gasket 60 which comprises a gasket ring 61 and a sponge ring 62 is compressed between the lower end of the plug 41 and the top surface of the wall 36; whereby the lower end of the plug 41 and the top surface of the wall 36 form a mechanical gasket 59 when they come into contact. In this way, the upper orifice 28 of the feed tube 17 is closed as shown in FIGS. 1 and 2. In a more simple embodiment the hydraulic gasket 60 can be absent. In this case, the orifice 22 can be closed simply by the lower end of the plug 41 when this plug is screwed downwards. In a preferred embodiment, when the position of the plug 41 is as shown in FIGS. 1 and 2, the annular disk 48 of the lid 11 closes the opening 29 of the compartment 26. FIG. 2 shows the closing of the orifice 28 by the plug 41, and the closing of the opening 29 of the compartment 26 by the annular disc 48 of the lid 11. In a preferred embodiment, these two closing operations take place simultaneously.

Figure 4:
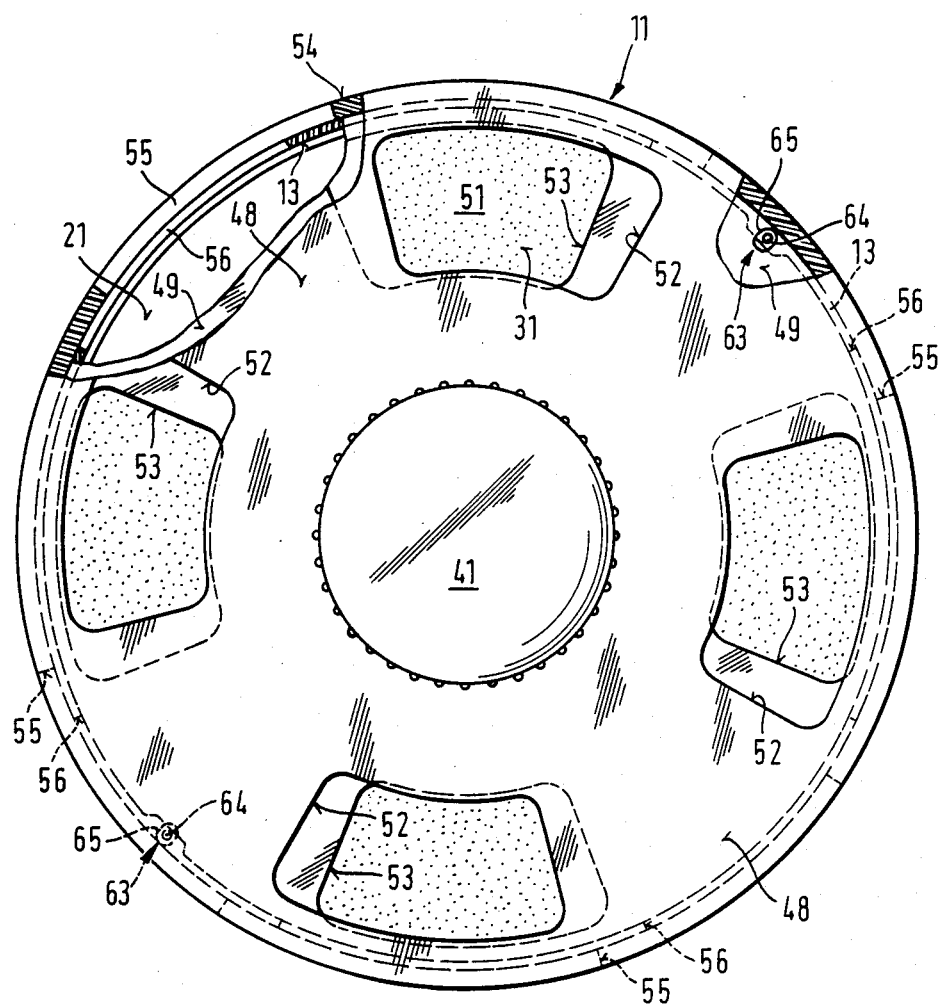
FIG. 4 illustrates a top view fo the apparatus according to FIG. 1.

The annular disk 48 of the lid 11 has several windows 52 which can be of the shape shown in FIG. 4. By rotating the annular disk 48 relative to the vessel, it is possible to position the windows 52 so that they are partially or completely superposed over the wondows 53 of the annular disk 49, which is inserted between the vessel 12 and the lid 11. When these windows coincide completely, the open area of the lid is approximately 50% of the total area covered by the lid 11. If the windows 52 and the windows 53 do not coincide, even partially, the annular disks 48 and 49 form a virtually sealed assembly which has no opening towards the top.

The upper portion of the side wall 13 of the vessel 12 also has windows 56 arranged along the cylindrical periphery of the said wall. The cylindrical flange 54 of the lid 11 also has windows 55. By rotating the annular disk 48 of the lid 11, it is possible to bring the windows 55 of the cylindrical flange of the lid 11 into partial or complete coincidence with the windows 56 of the wall 13 of the vessel. In this way, it is possible to adjust the lateral aeration of the compartment 51 in which the impregnation member 31 is situated. If the windows 55 and 56 do not coincide, the side wall 13 of the vessel is completely closed.

By virtue of the windows 52, 53, 55, 56, which have just been described, it is hence possible to adjust the aeration of the compartment 51 over a wide range of variation between total closure of this compartment towards the outside, and maximal opening of the said compartment towards the outside when the windows 56 of the vessel coincide fully with the windows 55 of the lid, and the windows 52 of the lid 11 coincide fully with the windows 53 of the annular disk 49.

The embodiment shown in FIGS. 1–4 includes means 63, shown in FIGS. 1 and 4, for preventing rotation of the disk 49 with respect to the wall 13 of the vessel 12 when the disk 48 is rotated. The means 63 comprise pins 64 on the wall 13 and slots 65 in the disk 49. As shown in FIGS. 1 and 4, the pins 64 are inserted in the slots 65.

The plug 41 has a cylindrical edge which rests on an annular surface of the disk 48 so that, when the plug 41 is screwed on the neck 22, the plug pushes the disk 48 and thereby the lid 11 downwards.

The plug 41 and the disk 48 of the lid 11 can be manufactured integrally or they can be independent parts, the plug 41 in this case being inserted in a circular opening in the centre of the disk 48. The latter embodiment has the advantage that the disk 48 can be rotated independently of the plug 41. It is thus possible to modify the degree of aeration of the compartment 51 without the need to modify either the position of the plug 41, with respect to the neck 22, or the position of the disk 48 of the lid 11, with respect to the opening 29 of the compartment 26.

The evaporating apparatus can, in addition, include a ratchet mechanism (not shown in the FIGS.) for drawing attention to the closing and/or opening fo the orifice 28, and preferably also the closing and/or opening of the opening 29.

The pitch of the internal thread 42 of the plug 41 and the external thread 24 of the neck 22 is such that a rotation through an angle of between 30° and 180° in a given direction is sufficient to open the orifice 28 and, if desired, simultaneously also the opening 29, and that a rotation through the same angle in the opposite direction is sufficient to seal simultaneously and hermetically the said orifice and, if desired, simultaneously also the said opening.

A method of operation of the evaporating apparatus described above is as follows:

The plug 23 is removed from the neck 22, a certain volume of the evaporable solution 18 is introduced into the reservoir 16 through the neck, and the latter is closed with the plug 23.

To transfer a portion of the solution 18 from the reservoir 16 to the compartment 26, the procedure is as follows:

The plug 41 is unscrewed by rotating it through an angle of between 30° and 180° in order to open the orifice 28 of the feed tube 17. Preferably, this also enables the opening 29 of the compartment 26 to be opened. An external pressure is then exerted on the walls of the reservoir 16, preferably a vertical or lateral pressure on the side walls 13 of the vessel 12, in order to cause a portion of the solution 18 to rise through the feed tube 17 and the orifice 28, and thereby to transfer such a portion 34 to the compartment 26 (in FIG. 3 the flow of liquid throuugh the feed tube 17, through the sponge 62, and into the compartment 26 is illustrated with arrows). When this transfer has been accomplished, the orifice 28 is closed with the plug 41, and the opening 29 is preferably also closed with the disk 48, by rotating the plug 41 in the appropriate direction.

During the time intervals between the intermittent transfers of portions of the solution, the orifice 28 and preferably also the opening 29 are kept closed. In the way, the solution contained in the reservoir 16 or in the compartment 26 is prevented from accidently flowing out of the evaporating apparatus, e.g., during transport of the latter.

As illustrated with arrows in FIG. 3, the portion of solution 34 contained in the compartment 26 gradually and continuously flows through the orifice 32 and the layer of fibrous material 33 to the impregnation member 31. The solution impregnated on this component evaporates through the windows 52, 53, 55, 56 described above. This is illustrated by dash line arrows in FIG. 3.

The user hence has the possibility of transferring portions of solutions from the reservoir 16 to the compartment 26 intermittently whenever he judges this to be necessary, or when he observes that the solution contained in the compartment 26 is depleted. To facilitate this observation, the disk 48 of the lid 11 and the disk 49 are preferably transparent.

In the context of the invention, the solution to be evaporated may be, e.g., a perfume. The latter may be used:

in the pure state, or
diluted with one or more solvents, or
diluted with a mixture of water with one or more solvents, or
diluted with a mixture of water with one or more solvents and with a surfactant.

The perfume or the solution containing the perfume may, in addition, contain other commonly used additives such as, for example, a fungicide, a coloring, an agent for preventing the ignition of the solution (an agent of this kind is commonly known as a fire retardant), and the like.

I claim:

1. A method for the evaporation of a solution which comprises:
    (a) introducing a certain volume of said solution (18) into a reservoir (16) having at least one elastic wall (13);
    (b) intermittently opening a passage (17,18) connecting said reservoir and a first compartment (26) outside said reservoir, for the transfer of a portion of said solution from said reservoir to said first compartment;
    (c) intermittently opening an opening (29) in said first compartment to the ambient air;
    (d) exerting an external pressure on said elastic wall of said reservoir, when said opening (29) and said passage (17,18) are open, sufficient to transfer said portion of said solution from said reservoir to said first compartment, and gradually and continuously transferring a portion of the solution (34) contained in said first compartment to an impregnation member (31) consisting of a material capable of absorbing a liquid, said member being placed on a support (21) outside said reservoir and outside said first compartment;
    (e) closing said opening of said first compartment and closing said passage; and
    (f) keeping said opening and said passage closed during the time intervals between intermittent transfers of portions of said solution from said reservoir to said first compartment.

2. A method, according to claim 1, wherein the opening of said opening (29) and of said passage (17,28) take place simultaneously, and the closing of said opening (29) and of said passage (17,28) take place is simultaneously.

3. A device for the evaporation of a solution which comprises:
    (a) a vessel (12) having a reservoir (16) designed to contain a certain volume of said solution (18), said reservoir having at least one elastic wall (13);
    (b) a first compartment (26) outside said reservoir, said first compartment having an opening (29) to the ambient air;
    (c) a passage (17,28) for the transfer of a portion of said solution from said reservoir to said first compartment;
    (d) a removable lid (11) having means for opening and closing, respectively, said passage for said transfer of said portion of said solution, thereby permitting and preventing, respectively, said transfer;
    (e) an impregnation member (31) placed on a support (21) outside said reservoir and outside said first compartment; and
    (f) means for gradually and continuously transferring the solution (34) contained in said first compartment to said impregnation member.

4. A device for the evaporation of a solution which comprises:
    (a) a vessel (12) having a reservoir (16) designed to contain a certain volume of said solution (18), said reservoir having at least one elastic wall (13);
    (b) a first compartment (26) outside said reservoir, said first compartment having an opening (29) to the ambient air;
    (c) means for opening and closing, respectively, said opening of said first compartment to the ambient air;
    (d) a passage (17,28) for the transfer of a portion of said solution from said reservoir to said first compartment;
    (e) means for opening and closing, respectively, said passage for said transfer of said portion of said solution, thereby permitting and preventing, respectively, said transfer;
    (f) an impregnation member (31) placed on a support (21) outside said reservoir and outside said first compartment; and,
    (g) means for gradually and continuously transferring the solution (34) contained in said first compartment to said impregnation member.

5. A device, according to claim 4, which further comprises a removable lid (11) having means for closing said passage for said transfer of said solution from said reservoir to said first compartment, and for closing said opening of said first compartment to the ambient air.

6. A device according to claim 3, wherein said impregnation member is placed in a second compartment (51) outside said reservoir and outside said first compartment; and said reservoir, said first compartment, and said second compartment form a compact structure contained in said vessel.

7. A device, according to claim 6, wherein
    (a) said vessel further comprises
        (i) an outer side wall (13)
        (ii) a support plate (21) which divides the inside of said vessel, into a lower portion and an upper portion;
    (b) said reservoir occupies said lower portion of said vessel;
    (c) said support plate further comprises a neck (22) which is the neck of said reservoir and which extends upwards from the central poriton of said support plate; and
    (d) the space enclosed between said outer side wall of said vessel and the outer wall of said neck in said upper portion of said vessel is divided into two compartments, an inner compartment and an outer compartment, said inner compartment being said first compartment having an outer wall (25) and said outer compartment being said second compartment.

8. A device, according to claim 7, wherein
    (a) said reservoir has a bottom (14);
    (b) said support plate has a bore (27), said bore being close to said neck; and
    (c) said passage for said transfer of said solution from said reservoir to said first compartment has a feed tube (17) having an upper orifice (28), said tube extending from a point close to said bottom of said reservoir to said bore in said support plate, the upper end of said tube being inserted into said bore.

9. A device, according to claim 8, wherein
(a) said first compartment has a base wall (35) placed on a layer (33) of a fibrous material capable of absorbing a liquid, said layer being placed between said base wall and said support plate, said layer being in contact with said impregnation member; and
(b) said base wall has an orifice (32) enabling said solution contained in said first compartment to flow to said layer and thence to flow to said impregnation member, said orifice being at at level below said upper orifice of said tube when said bottom of said vessel is in the horizontal position.

10. A device, according to claim 8, further comprising a removable lid (11) having a plug (41) which has an internal thread (42) enabling said plug to be screwed on said neck, said neck having an external thread (24) which corresponds to said internal thread of said plug; said different constituent parts being arranged such that, when said plug is screwed on said neck, said lid comes into contact with said outer wall of said first compartment, and thereby closes said opening of said first compartment at the same time as the lower end of said plug comes into contact with a surface of said support plate, and thereby closes said upper orifice of said feed tube.

11. A device according to claim 10, wherein the pitch of said internal thread and of said external thread is such that a rotation through an angle of between 30° and 180° in a given direction is sufficient to simultaneously open said passage and said opening, and a rotation through the same angle in the opposite direction is sufficient to simultaneously close and hermetically seal said passage and said opening.

* * * * *